(12) United States Patent  (10) Patent No.: US 9,033,871 B2
Schara et al.  (45) Date of Patent: May 19, 2015

(54) GRAVITY REFERENCED ENDOSCOPIC IMAGE ORIENTATION

(75) Inventors: Nathan Jon Schara, Pasadena, CA (US); Hans David Hoeg, Arcadia, CA (US); Eric Lawrence Hale, Altadena, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 1533 days.

(21) Appl. No.: 11/053,531

(22) Filed: Feb. 8, 2005

(65) Prior Publication Data

US 2005/0228230 A1    Oct. 13, 2005

Related U.S. Application Data

(60) Provisional application No. 60/560,172, filed on Apr. 7, 2004.

(51) Int. Cl.
*A61B 1/06* (2006.01)
*A61B 1/00* (2006.01)
*A61B 1/04* (2006.01)

(52) U.S. Cl.
CPC .............. *A61B 1/042* (2013.01); *A61B 1/00045* (2013.01); *A61B 2562/0219* (2013.01)

(58) Field of Classification Search
CPC .......... A61B 1/00174; A61B 1/00179; A61B 1/00181; A61B 1/00183; A61B 1/042; A61B 1/00057; A61B 1/00177; A61B 2562/0219
USPC ............. 600/117, 118, 112, 109, 173, 65, 74, 600/104, 114, 170, 171, 129, 161, 164, 176, 600/137, 145; 348/65, 74, 289
See application file for complete search history.

(56) References Cited

U.S. PATENT DOCUMENTS

| | | | |
|---|---|---|---|
| 3,572,325 A | 3/1971 | Bazell et al. ....................... 128/6 |
| 3,880,148 A | 4/1975 | Kanehira et al. .................. 128/6 |
| 4,697,577 A | 10/1987 | Forkner ............................. 128/6 |
| 4,802,461 A * | 2/1989 | Cho ............................... 600/108 |
| 5,230,623 A | 7/1993 | Guthrie et al. ................... 433/72 |
| 5,307,804 A | 5/1994 | Bonnet ............................... 126/7 |
| 5,313,306 A | 5/1994 | Kuban et al. .................... 348/65 |
| 5,531,227 A | 7/1996 | Schneider .................. 128/653.1 |
| 5,617,857 A | 4/1997 | Chader et al. ............. 128/653.1 |
| 5,621,830 A * | 4/1997 | Lucey et al. .................... 385/25 |
| 5,623,560 A | 4/1997 | Nakajima et al. ............. 382/295 |
| 5,661,519 A | 8/1997 | Franetzki ........................ 348/66 |
| 5,677,763 A | 10/1997 | Redmond ....................... 356/73 |
| 5,899,851 A | 5/1999 | Koninckx ...................... 600/117 |

(Continued)

FOREIGN PATENT DOCUMENTS

JP   403118019 A  *  5/1991
JP   6269403         9/1994

(Continued)

*Primary Examiner* — Anhtuan T Nguyen
*Assistant Examiner* — Timothy J Neal
(74) *Attorney, Agent, or Firm* — St. Onge Steward Johnston & Reens LLC

(57) ABSTRACT

An endoscope having a longitudinal axis, a view vector angularly offset from said longitudinal axis, an accelerometer, and an image rotator effectively responsive to said accelerometer, wherein said accelerometer is arranged for measuring rotations about a measurement axis which is generally parallel to said view vector. Through the use of this apparatus, an image is maintained in an upright orientation.

21 Claims, 3 Drawing Sheets

(56) References Cited

U.S. PATENT DOCUMENTS

| | | | |
|---|---|---|---|
| 5,920,395 A | 7/1999 | Schulz | 356/375 |
| 5,954,634 A | 9/1999 | Igarashi | 600/109 |
| 5,976,076 A | 11/1999 | Kolff et al. | 600/166 |
| 6,007,484 A | 12/1999 | Thompson | 600/173 |
| 6,097,423 A * | 8/2000 | Mattsson-Boze et al. | 348/65 |
| 6,167,296 A | 12/2000 | Shahidi | 600/427 |
| 6,275,724 B1 * | 8/2001 | Dickinson et al. | 600/424 |
| 6,371,909 B1 | 4/2002 | Hoeg et al. | 600/173 |
| 6,442,417 B1 | 8/2002 | Shahidi et al. | 600/429 |
| 6,464,631 B1 | 10/2002 | Girke et al. | 600/109 |
| 6,471,637 B1 * | 10/2002 | Green et al. | 600/109 |
| 6,500,115 B2 | 12/2002 | Krattiger et al. | 600/173 |
| 6,648,817 B2 | 11/2003 | Schara et al. | 600/173 |
| 6,663,559 B2 | 12/2003 | Hale et al. | 600/118 |
| 6,695,774 B2 | 2/2004 | Hale et al. | 600/173 |
| 6,868,356 B2 * | 3/2005 | Nai et al. | 702/95 |
| 2002/0045855 A1 | 4/2002 | Frassica | 604/109 |
| 2002/0099263 A1 * | 7/2002 | Hale et al. | 600/117 |
| 2002/0161280 A1 | 10/2002 | Chatenever et al. | 600/112 |
| 2003/0016883 A1 | 1/2003 | Baron | 382/289 |
| 2004/0127769 A1 | 7/2004 | Hale et al. | 600/173 |
| 2004/0210105 A1 | 10/2004 | Hale et al. | 600/101 |
| 2005/0020883 A1 * | 1/2005 | Chatenever et al. | 600/173 |
| 2005/0027167 A1 | 2/2005 | Chatenever et al. | 600/173 |
| 2005/0054895 A1 | 3/2005 | Hoeg et al. | 600/117 |
| 2005/0113643 A1 | 5/2005 | Hale et al. | 600/118 |
| 2005/0154260 A1 | 7/2005 | Schara et al. | 600/173 |
| 2005/0187432 A1 | 8/2005 | Hale et al. | 600/117 |

FOREIGN PATENT DOCUMENTS

| | | |
|---|---|---|
| WO | WO 95/01749 | 1/1995 |
| WO | WO 01/22865 | 4/2001 |

* cited by examiner

GRAVITY REFERENCED ENDOSCOPIC IMAGE ORIENTATION

CROSS-REFERENCE TO RELATED APPLICATIONS

This application claims the benefit of U.S. provisional application Ser. No. 60/560,172 filed on Apr. 7, 2004, entitled "Gravity referenced endoscopic image orientation", the contents of which are incorporated herein by reference.

STATEMENT REGARDING FEDERALLY SPONSORED RESEARCH

Not Applicable

FIELD OF THE INVENTION

The present invention relates to endoscopes (including devices such as borescopes, fiberscopes, etc.) in which the rotational orientation of the endoscopic image is presented in its actual relationship to the viewer's reference frame.

BACKGROUND OF THE INVENTION

Many endoscopes view only directly forward. Others feature fixed or movable reflectors in the distal portion to allow off-axis viewing. Some, most commonly flexible types, feature actuated bending portions at the distal end. This invention is applicable to all types of axial, non-axial, and variable direction of view endoscopes.

Today, typically a camera means, such as a CCD or CMOS chip, is attached to the endoscope. It receives the image from the image forwarding system in the endoscope and produces a signal for a screen to display the endoscopic image. The surgeon observes this screen while manipulating the endoscope. A surgical or diagnostic procedure generally requires the surgeon to pitch the endoscope about a lateral axis or roll it about a longitudinal axis. As these manipulations occur to an endoscope with an attached camera, the camera faithfully relates what it sees, with its own upright axis displayed as the upright axis of the image on the display. This often results in rotation of the viewed image.

This is the very problem. When the image is displayed on the screen and the endoscope is manipulated, it is as though the surgeon must tilt his head to follow the rotating image. However, the surgeon is standing up, and the rotating image can be confusing to him. What he really wants to see on the screen is an image that is oriented the same as he would see it if he were inside the examination site, standing up, with the same upright orientation.

A solution to this problem is proposed in U.S. Pat. No. 5,307,804 to Bonnet (1994), which is incorporated herein by reference in its entirety. An object of this invention was to maintain the orientation of an endoscopic image without the use of electronic sensing and positioning devices. A pendulum fixed to a camera is rotatably attached to an endoscope. The pendulum maintains an orientation with respect to gravity around the endoscope longitudinal axis. As the endoscope rotates, the pendulum causes the camera to rotate in the opposite direction relative to the endoscope. This is intended to maintain the image in a proper orientation.

An endoscope with rotational orientation correction is also suggested in U.S. Pat. No. 5,899,851 to Koninckx (1999), which is incorporated herein by reference in its entirety. An electronic rotation pick-up means responsive to gravity senses rotation of a camera around the endoscope longitudinal axis. An image rotator rotates the camera image according to the rotation signal from the rotation pick-up means.

Another endoscope and camera system with rotational orientation correction is disclosed in U.S. Pat. No. 6,097,423 to Mattsson-Boze, et al. (2000), which is incorporated herein by reference in its entirety. Electronic sensing and positioning devices combine to sense and correct the rotation of a camera rotatably attached to an endoscope. An accelerometer fixed to the camera serves as an electronic rotation pick-up means responsive to gravity. A motor rotates the camera according to signals from the accelerometer. This accelerometer and motor system is functionally equivalent to the pendulum described by Bonnet. While the pendulum relies on the force of gravity to rotate, the small accelerometer sensitively measures gravity and the motor rotates the assembly accordingly. The system can therefore be thought of as an electro mechanical pendulum. Mattsson-Boze also recognizes rotation of the image by electronic manipulation to correct the image orientation, but actively discourages this practice for several reasons.

U.S. Pat. No. 6,471,637 to Green, et al. (2002), which is incorporated herein by reference in its entirety, discloses the same apparatus as disclosed in Mattsson-Boze, and suggests two alternative methods for image rotation. In the first method, an optical image rotator is used instead of a rotating camera. In the second method, electronic manipulation is used to correct the image orientation. Also, one or more gyroscopes are suggested as alternative electronic rotation pick-up means.

U.S. patent application Ser. No. 10/093,650 by Chatenever, et al. (2002), which is incorporated herein by reference in its entirety, discloses the same apparatus as disclosed in Mattsson-Boze and in Green, and suggests two alternative methods for electronic rotation pick-up. In the first method, image analysis is used to compute a rotational signal. In the second method, a machine vision system is used to compute a rotation signal.

All of the above solutions compensate only for roll about the longitudinal axis and provide a rotationally corrected image for axial viewing endoscopes. They also provide an approximation of the correct orientation for slightly oblique viewing endoscopes held near horizontal. None of the above disclosures suggest a solution that works for significantly oblique, side, or retro viewing endoscopes.

Oblique, side, or retro viewing endoscopes require a solution that takes into account the off-axis viewing direction. Variable direction-of-view endoscopes further complicate the situation. In response to this need, U.S. patent application Ser. No. 10/754,130 by Schara, et al. discloses a method which provides a general solution applicable for all angles of pitch and roll, and for all endoscopic viewing angles.

While comprehensive, this solution relies on mathematical parameterizations and computations taking into account endoscope pitch, roll, and viewing angle to obtain the required amount of rotational image compensation. It would be desirable to obtain a direct solution to the image leveling problem for off-axis and variable direction of view endoscopes without the need for computations requiring information about the endoscope attitude and viewing angle.

Accordingly, it is an object of this invention to provide a means for maintaining the proper upright orientation (with respect to the viewer) of a viewed image from an off-axis or variable direction of view endoscope without the need for complicated computations.

BRIEF SUMMARY OF THE INVENTION

In an endoscope having a longitudinal axis, a view vector angularly offset from said longitudinal axis, an accelerometer, and an image rotator effectively responsive to said accelerometer, the improvement comprising said accelerometer arranged for measuring rotations about a measurement axis which is generally parallel to said view vector.

DETAILED DESCRIPTION OF THE INVENTION

The following detailed description illustrates the invention by way of example, not by way of limitation of the principles of the invention. This description will clearly enable one skilled in the art to make and use the invention, and describes several embodiments, adaptations, variations, alternatives and uses of the invention, including what we presently believe is the best mode of carrying out the invention.

Figure 1:
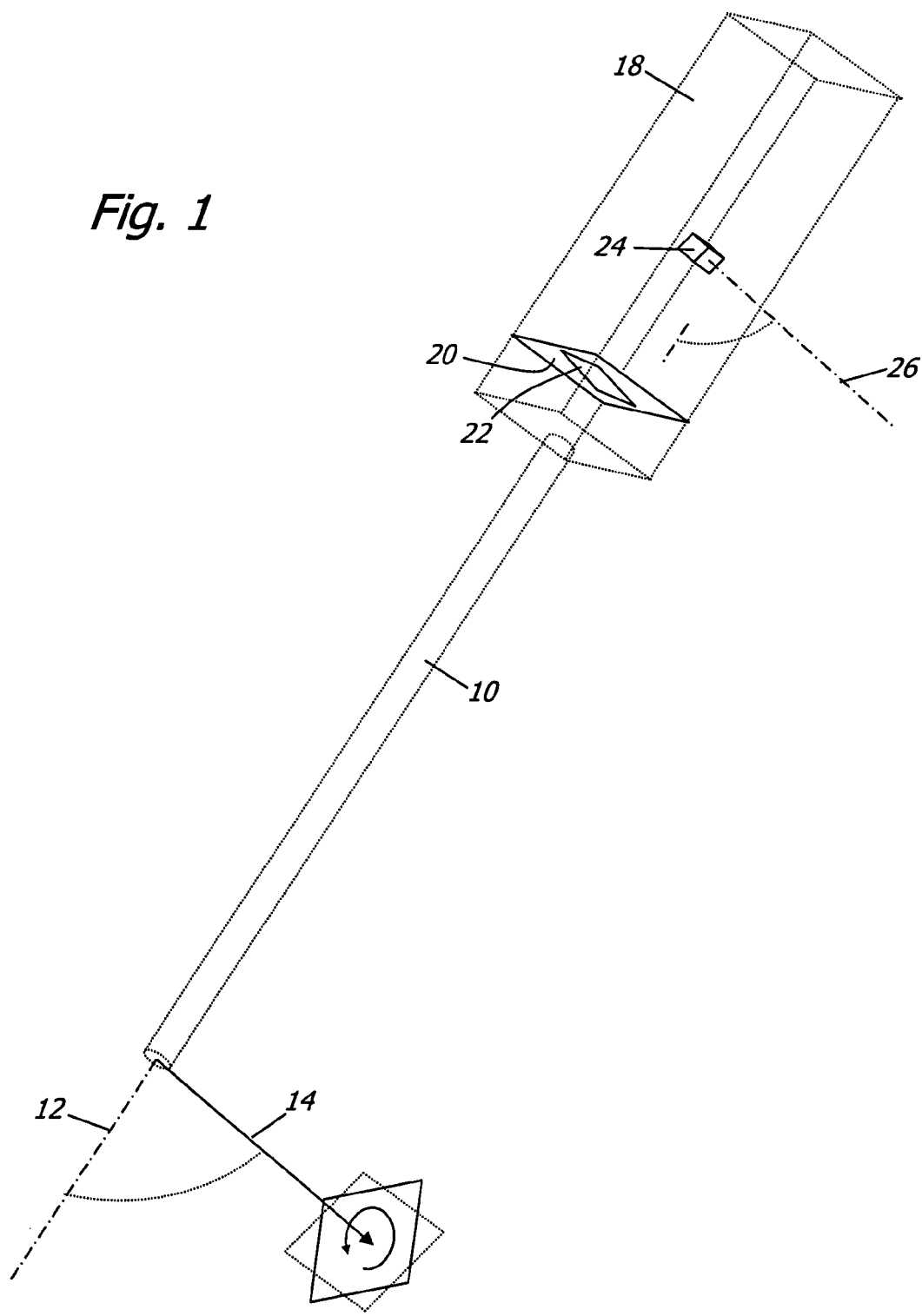
FIG. 1 shows the preferred embodiment of the present invention for an endoscope with a fixed off-axis view.

FIG. 1 shows a first embodiment of the invention. The endoscope includes a shaft 10 that contains elements that are conventionally provided. The shaft has a longitudinal axis 12. An objective optical system is provided at the distal end of the shaft to give the endoscope a view vector 14 that is angularly offset from the longitudinal axis 12. The objective optical system comprises components such as lenses, prisms, reflectors, etc.

A housing 18 is provided at the proximal end of the shaft 10. An image sensing device or camera 20 is mounted in the housing 18. It is configured to receive images 22 from the objective optical system.

A rotation pick-up means 24 is mounted in the housing 18 about an axis 26 parallel to the view vector 14. The rotation pick-up means 24 may comprise two accelerometers. Each accelerometer measures a component of gravity along a particular measurement axis. Changes in the gravitational force measurements from the accelerometers are related to rotations of the endoscope. Aligning this rotation measurement device 24 with the parallel axis 26 captures the mathematical relations of U.S. patent application Ser. No. 10/754,130 by Schara, et al. in the geometry of the apparatus. This makes it possible to circumvent most of the rotation correction calculations required in Schara, et al.

The housing 18 also encases an electronic processor (not shown). The processor is in communication with the rotation pick-up means 24. The accelerometers provide pulse-width-modulated signals to the processor which can convert each signal into a gravitational force measurement. The processor is also in communication with an image rotator which may comprise, for example a rotating camera 20.

The image rotator effectively rotates the image via electronic processing of the image captured by the camera. The image rotator is directed by the processor to rotate the image 22 by the amount determined by the rotation pick-up means 24. In this way the image is effectively rotated to a desired orientation relative to a local vertical.

Figure 2A:
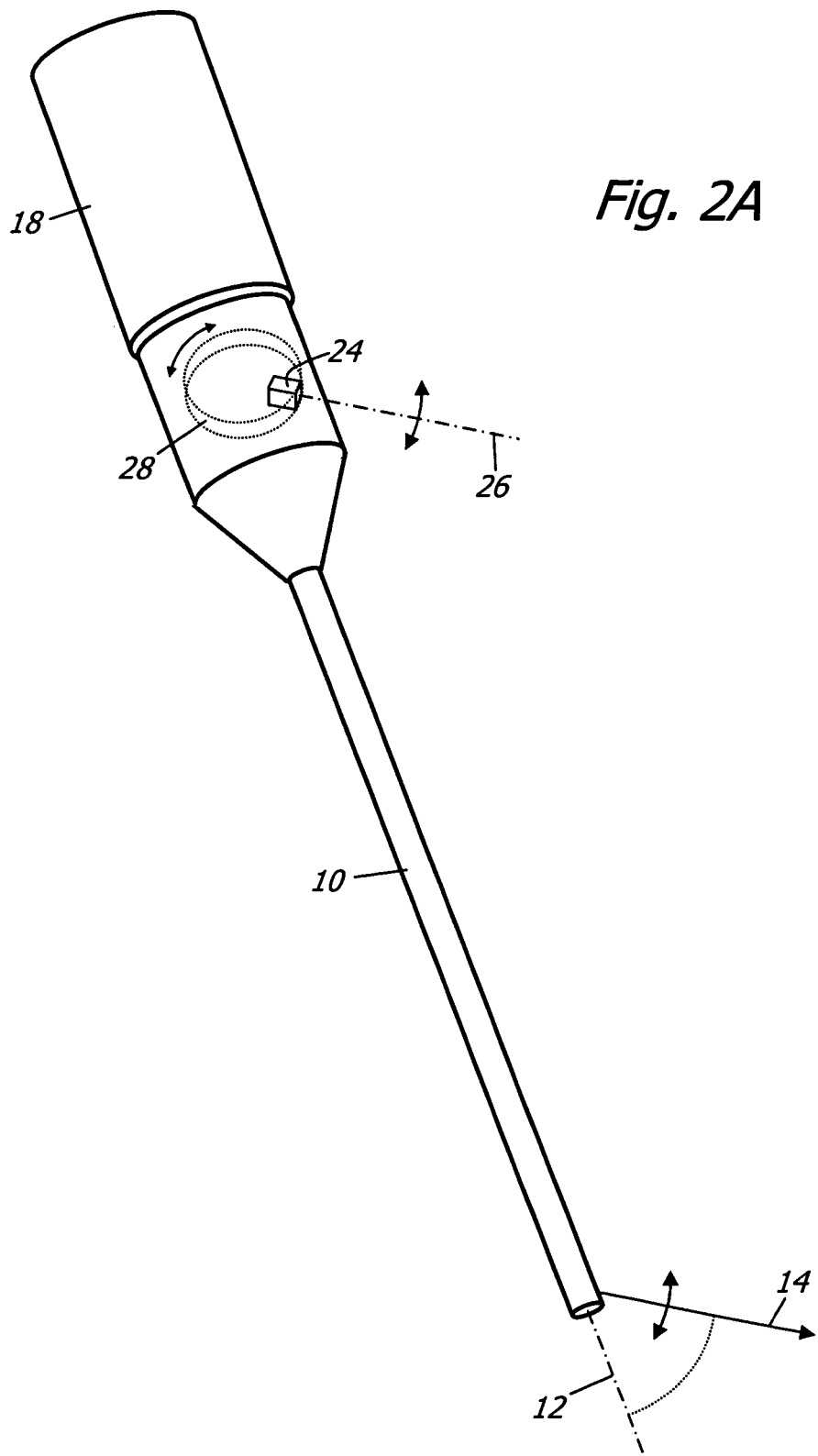
FIGS. 2A and 2B show preferred embodiments of the present invention for endoscopes with variable viewing directions.

FIG. 2A illustrates the principle of the present invention applied to a rigid variable direction of view endoscope. In this case the parallel axis 26 is pivotable and moves in conjunction with the view vector 14. The pick-up means 24 is mounted in an actuation knob 28 coupled to the view vector 14 by a mechanical drive system (not shown). By rotating the knob 28 a user changes the endoscopic line of sight and changes the attitude of the rotation pick-up means 24 correspondingly.

The knob 28 could be any type of lever or pointer, such as those disclosed in U.S. Pat. No. 6,695,774 to Schara, et al. It is also possible to use a joystick or buttons, located remotely or on the endoscope. These input devices can actuate the view vector 14 and the rotation pick-up means 24 through motors and an internal mechanism.

Figure 2B:
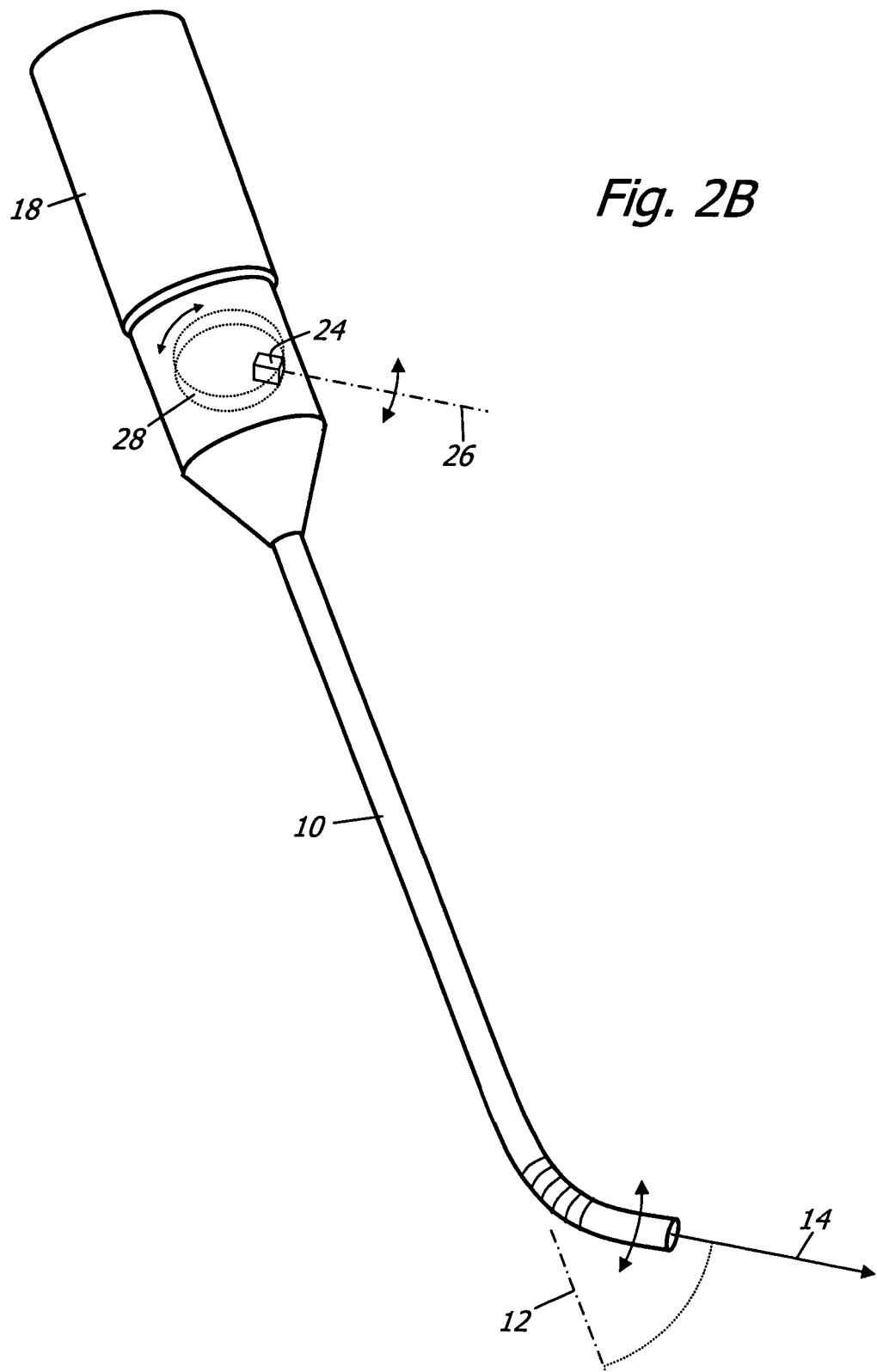

FIG. 2B shows these principles applied to a rigid variable direction of view endoscope with a flexible tip. In this case the tip deflection corresponds to the alignment of the rotation pick-up means 24 such that the view vector 14 and the parallel axis 26 are always parallel.

Image rotation can be accomplished in one or more of four ways: physical rotation of the image sensor 20; optical rotation of the received image 22 prior to incidence upon the image sensor 20; electronic rotation of the image 22 within a processor; and rotation of all or part of the display device. The details of these methods are described in Chatenever and other prior art.

The electronic rotation pick-up means can be embodied in a variety of ways. Accelerometers responsive to the force of gravity, such as those described in Koninckx and Mattson-Bose, are used in the preferred embodiment. Any sensor capable of detecting the direction of a local vertical could also be used.

The present invention has been described above in terms of a presently preferred embodiment so that an understanding of the present invention can be conveyed. However, there are many alternative arrangements for a method for providing gravity referenced endoscopic image orientation not specifically described herein but with which the present invention is applicable. For example, while the examples were given with respect to endoscopes for use in surgical procedures, the present invention is equally applicable with respect to borescopes or the like for use within various mechanical structures. Therefore, the term "endoscope" as used herein, refers to an endoscope (used for medical procedures) or any similar device such as a borescope, a fiberscope, etc.

This invention is not to be limited by the embodiments shown in the drawings and described in the description, which are given by way of example and not of limitation, but only in accordance with the scope of the appended claims.

We claim:

1. A system for orienting an endoscopic image, comprising an endoscope having a longitudinal axis, a view vector angularly offset from said longitudinal axis, a rotation pick-up device, and an image rotator responsive to said rotation pick-up device, wherein said rotation pick-up device is arranged for measuring rotations of the endoscope about an axis which is generally parallel to said view vector; and wherein said axis generally parallel to said view vector is longitudinally offset from said view vector; and
   wherein said rotation pick-up device is disposed in a housing on a proximal end of said endoscope such that said longitudinal axis passes through the rotation pick-up device.

2. The system of claim 1, wherein said rotation pick-up device comprises an accelerometer.

3. The system of claim 1, wherein said image rotator comprises a rotating camera.

4. The system of claim 1, wherein said image rotator comprises an electronic processor.

5. The system of claim 1, wherein said image rotator comprises an optical image rotator.

6. The system of claim 1, wherein said endoscope is generally rigid.

7. A system for orienting an endoscopic image, comprising an endoscope having a longitudinal axis, a variable view vector that is offset from said longitudinal axis at an angle that changes relative to said longitudinal axis, a rotation pick-up device, and an image rotator responsive to said rotation pick-up device, wherein said rotation pick-up device is arranged for measuring rotations of the endoscope about an axis which remains generally parallel to said view vector as the angle at which the view vector is angularly offset from said longitudinal axis changes; and wherein said axis which remains generally parallel to said view vector is longitudinally offset from said view vector; and wherein said rotation pick-up device is disposed in a housing on a proximal end of said endoscope such that said longitudinal axis passes through the rotation pick-up device.

8. The system of claim 7, wherein said rotation pick-up device comprises an accelerometer.

9. The system of claim 7, wherein said image rotator comprises a rotating camera.

10. The system of claim 7, wherein said image rotator comprises an electronic processor.

11. The system of claim 7, wherein said image rotator comprises an optical image rotator.

12. The system of claim 7, wherein said endoscope is generally rigid.

13. The system of claim 12, wherein the distal portion of said endoscope is generally flexible.

14. A system for orienting an endoscopic image, comprising an endoscope having a longitudinal axis, a variable view vector that extends from the distal end of the endoscope at an angle relative to said longitudinal axis, a rotation pick-up device that measures rotations of the endoscope about a measurement axis angularly offset from said longitudinal axis at the same angle as said view vector, and an image rotator responsive to said rotation pick-up device, wherein said measurement axis remains generally parallel to said view vector as the angle of said view vector relative to said longitudinal axis varies; and wherein said axis which remains generally parallel to said view vector is longitudinally offset from said view vector; and wherein said rotation pick-up device is disposed in a housing on a proximal end of said endoscope such that said longitudinal axis passes through the rotation pick-up device.

15. The system of claim 14, wherein said rotation pick-up device comprises an accelerometer.

16. The system of claim 14, wherein said image rotator comprises a rotating camera.

17. The system of claim 14, wherein said image rotator comprises an electronic processor.

18. The system of claim 14, wherein said image rotator comprises an optical image rotator.

19. The system of claim 14, wherein said endoscope is generally rigid.

20. The system of claim 19, wherein the distal portion of said endoscope is generally flexible.

21. A system for orienting an endoscopic image, comprising an endoscope having a longitudinal axis, a view vector not parallel to said longitudinal axis, a rotation pick-up device, and an image rotator responsive to said rotation pick-up device, wherein said rotation pick-up device is arranged for measuring rotations of the endoscope about an axis which is generally parallel to said view vector; and wherein said axis which remains generally parallel to said view vector is longitudinally offset from said view vector;

wherein said rotation pick-up device is disposed in a housing on a proximal end of said endoscope such that said longitudinal axis passes through the rotation pick-up device.

\* \* \* \* \*